(12) United States Patent
Butterfield et al.

(10) Patent No.: US 11,395,645 B2
(45) Date of Patent: Jul. 26, 2022

(54) RETRACTORS

(71) Applicant: SURE RETRACTORS LIMITED, Cumbernauld Glasgow (GB)

(72) Inventors: Forbes Butterfield, Corby Northamptonshire (GB); Colin Crosland, Edinburgh Lothian (GB); Kenneth McCorkindale, Edinburgh Lothian (GB); Lewis Kingsley, Edinburgh Lothian (GB)

(73) Assignee: SURE RETRACTORS LTD, Glasgow (GB)

( * ) Notice: Subject to any disclaimer, the term of this patent is extended or adjusted under 35 U.S.C. 154(b) by 134 days.

(21) Appl. No.: 16/759,685

(22) PCT Filed: Nov. 5, 2018

(86) PCT No.: PCT/GB2018/053199
§ 371 (c)(1),
(2) Date: Apr. 27, 2020

(87) PCT Pub. No.: WO2019/086901
PCT Pub. Date: May 9, 2019

(65) Prior Publication Data
US 2020/0337689 A1    Oct. 29, 2020

(30) Foreign Application Priority Data
Nov. 3, 2017  (GB) ...................................... 1718242

(51) Int. Cl.
*A61B 17/02* (2006.01)
*A61B 17/00* (2006.01)
(52) U.S. Cl.
CPC ...... *A61B 17/0206* (2013.01); *A61B 2017/00407* (2013.01); *A61B 2017/0256* (2013.01)

(58) Field of Classification Search
CPC .............. A61B 17/0206; A61B 17/025; A61B 2017/0256; A61B 2017/0262; A61B 17/02; A61B 17/7052
See application file for complete search history.

(56) References Cited

U.S. PATENT DOCUMENTS

| 4,926,849 A | 5/1990 | Downey |
| 5,704,937 A | 1/1998 | Martin |

(Continued)

FOREIGN PATENT DOCUMENTS

| EP | 0951868 | 10/1999 |
| GB | 1008555 | 10/1965 |
| WO | 2014/018624 | 1/2014 |

OTHER PUBLICATIONS

Search Report for GB Application No. GB1718242.9.
International Search Report for International Application No. PCT/GB2018/053199.

*Primary Examiner* — Ellen C Hammond
(74) *Attorney, Agent, or Firm* — Liu & Liu (57) ABSTRACT

The invention relates to a retractor. The retractor comprises an elongate support member having a screw thread along at least part of its length and a first arm having a first anatomy engaging member depending therefrom. The retractor also comprises a second arm having a second anatomy engaging member depending therefrom and a threaded portion which cooperates with the screw thread to move the second arm along the support member. The retractor also comprises a driver operable to move the second arm along the support member by cooperation of the threaded portion and the screw thread whereby separation between the first and second arms changes. The retractor further comprises a bridging part attached towards a first end thereof to the first arm and attached towards a second, opposite end thereof to (Continued)

the second arm, the bridging part having a third anatomy engaging member depending therefrom.

17 Claims, 4 Drawing Sheets

(56) References Cited

U.S. PATENT DOCUMENTS

| | | | | |
|---|---|---|---|---|
| 5,779,629 | A * | 7/1998 | Hohlen | A61B 17/0293 |
| | | | | 600/233 |
| 6,102,854 | A | 8/2000 | Cartier et al. | |
| 9,028,522 | B1 | 5/2015 | Prado | |
| 9,084,591 | B2 * | 7/2015 | Reglos | A61B 17/0293 |
| 9,386,971 | B1 * | 7/2016 | Casey | A61B 17/7032 |
| 2004/0049188 | A1 * | 3/2004 | Slivka | A61B 17/7052 |
| | | | | 606/249 |
| 2010/0222644 | A1 | 9/2010 | Sebastian et al. | |
| 2012/0283521 | A1 | 11/2012 | Smith et al. | |
| 2013/0237766 | A1 | 9/2013 | Pell et al. | |
| 2015/0313642 | A1 * | 11/2015 | Fessler | A61B 17/7014 |
| | | | | 606/258 |
| 2018/0214189 | A1 * | 8/2018 | Olea | A61B 17/7077 |
| 2018/0271507 | A1 * | 9/2018 | Gasser | A61B 17/683 |

* cited by examiner

*Fig.5C*

RETRACTORS

FIELD OF THE INVENTION

The present invention relates to a retractor comprising a support member and two arms, the retractor being configured for movement along the support member of at least one of the two arms relative to the other arm.

BACKGROUND ART

Known retractors often comprise two arms which are movable in relation to each other by way of a scissors mechanism. GB 2547792 A describes an alternative form of retractor in which two arms are mounted on a support member with at least one of the two arms being movable along the support member by way of cooperating threaded profiles on the arm and the support member whereby separation between the two arms is changed.

The present inventors have devised an improvement to a retractor of the form described in GB 2547792 A which provides for increased capability. It is therefore an object for the present invention to provide an improved retractor in which two arms are mounted on a support member with at least one of the two arms being movable along the support member whereby separation between the two arms is changed.

STATEMENT OF INVENTION

According to a first aspect of the present invention there is provided a retractor comprising:
  an elongate support member having a screw thread along at least part of its length;
  a first arm having a first anatomy engaging member depending therefrom;
  a second arm having a second anatomy engaging member depending therefrom and a threaded portion which cooperates with the screw thread to move the second arm along the support member;
  a driver operable to move the second arm along the support member by cooperation of the threaded portion and the screw thread whereby separation between the first and second arms changes; and
  a bridging part attached towards a first end thereof to the first arm and attached towards a second, opposite end thereof to the second arm, the bridging part having a third anatomy engaging member depending therefrom.

The retractor comprises an elongate support member which defines a screw thread along at least part of its length. The support member may be straight. Furthermore, the support member may be of generally cylindrical form with the screw thread defined on the surface of the support member. The retractor further comprises first and second arms with a first anatomy engaging member depending from the first arm and a second anatomy engaging member depending from the second arm. Each of the first and second arms may extend away from the support member. At least one of the first and second arms may be straight. The second arm defines a threaded portion which engages with the screw thread to move the second arm along the support member. The retractor also comprises a driver which is operable, such as by a surgeon, to move the second arm along the support member by cooperation of the threaded portion and the screw thread whereby separation between the first and second arms changes. The retractor may be configured such that the first and second arms are parallel with each other and more specifically in alignment with each other.

The retractor further comprises a bridging part attached at a first end thereof to the first arm and attached at a second, opposite end thereof to the second arm, the bridging part having a third anatomy engaging member depending therefrom. The bridging part may be straight. The retractor may be configured such that the first and second arms and the bridging part lie in substantially the same plane.

The bridging part may be movable on the first and second arms while the bridging part remains attached to the first and second arms. The retractor is thus configured to provide for retraction along two different directions by way of the first to third anatomy engaging members. For example, retraction may be provided in a first direction extending between the first and second anatomy engaging members and in a second direction extending away from the third anatomy engaging member. The support member, first and second arms and the bridging part provide a stable support for the first to third anatomy engaging members. Furthermore, the configuration of the retractor provides for ease of change in separation of the first to third anatomy engaging members and more specifically progressive change in separation of the first to third anatomy engaging members.

The bridging part may be configured such that its length, i.e. separation between its first and second ends, is changeable. The length of the bridging part may therefore be changed as the separation between the first and second arms is changed. The bridging part may be telescopic. The bridging part may comprise a first bridging part component comprising the first end and a second bridging part component comprising the second end, the proximal end of the second bridging part component being telescopically received in the proximal end of the first bridging part component.

The bridging part may be configured to releasably attach at each of its first and second ends to a respective one of the first and second arms. Each of the first and second ends of the bridging part may define a bridging part profile which cooperates with a profile of the arm to resist separation of the bridging part from the arm whilst allowing movement of the bridging part along the arm. The bridging part profile may have a main profile portion which extends across a first surface of the arm, i.e. an upper surface of the arm when the retractor is in use. The main profile portion and the first surface of the arm may have corresponding shapes whereby the main profile portion and the first surface are adjacent and more specifically substantially contiguous. The bridging part profile may have first and second lateral portions at a respective end of the main profile portion which are each shaped to extend part way across a second surface of the arm, which is oppositely directed to the first surface. Distal ends of the first and second lateral portions may be spaced apart from each other whereby the bridging part profile does not encircle the arm with the distal end of the first lateral portion opposing the distal end of the second lateral portion. The bridging part profile may thus wrap around the arm without encircling the arm. The bridging part may be attached to an arm by sliding the bridging part profile over the distal end of the arm. Where the bridging part profile is defined by a resilient material, the bridging part may be clipped into place on an arm.

The retractor may be configured for movement of the bridging part along each of the first and second arms. The bridging part profile at each of the first and second ends of the bridging part may be shaped and the arms may be shaped, such as is described above, to allow for movement of the bridging part profile over its respective arm while the bridging part remains attached to the first and second arms. The retractor may comprise a ratchet mechanism to regulate movement of the bridging part along the arm. Teeth of the ratchet mechanism may be defined along at least a part of the arm. A pawl of the ratchet mechanism may be comprised in an end of the bridging part. The teeth of the ratchet mechanism may be configured to allow for movement of the pawl over the teeth in a first direction only. The teeth may be configured such that the pawl abuts against a face of each tooth in a second direction opposite the first direction whereby movement in the second direction is resisted. The bridging part may be configured such that the pawl may be moved apart manually from the teeth and against a spring bias towards the teeth. When the pawl is moved apart from the teeth, the bridging part may be moved in the second direction. The pawl may comprise a protrusion which is configured to be gripped by a user, such as between finger and thumb, whereby the pawl may be released from the teeth to allow movement of the bridging part in the second direction. The protrusion may extend from the bridging part and more specifically in a direction away from the arm. The pawl may be integrally formed with the bridging part with the pawl moving relative to the teeth of the arm by way of a living hinge.

The retractor may further comprise a second bridging part. The second bridging part may be attached towards a first end thereof to the first arm at a location spaced apart from the first bridging part. In addition, the second bridging part may be attached towards a second end thereof to the second arm at a location spaced apart from the first bridging part. The second bridging part may be movable on the first and second arms while the second bridging part remains attached to the first and second arms. The second bridging part may have a fourth anatomy engaging member depending therefrom. The retractor may be configured such that the first and second anatomy engaging members oppose each other and the third and fourth anatomy engaging members oppose each other. Retraction may therefore be in a first direction between the first and second anatomy engaging members and in a second direction between the third and fourth anatomy engaging members.

The retractor may be configured such that the first and second directions are substantially orthogonal. The retractor may be configured such that the first and second arms and the first and second bridging parts lie in substantially the same plane. The first and second arms and the first and second bridging parts may define a rectangular space between them.

The second bridging part and an arm may comprise a ratchet mechanism apart from the ratchet mechanism of the first bridging part. The ratchet mechanism may be of the same form and function as the ratchet mechanism of the first bridging part. As an exception, a first set of teeth for the ratchet mechanism of the first bridging part and a second set of teeth for the ratchet mechanism of the second bridging part may be oppositely directed.

The first and second sets of teeth may be configured to allow for movement of the pawls over their respective set of teeth in opposite directions. For example, where the first bridging part is closer to the proximal ends of the first and second arms, i.e. closer to the support member, than the second bridging part, the first set of teeth may be configured to allow movement of the first bridging part towards the support member when its pawl is engaged and the second set of teeth may be configured to allow movement of the second bridging part away from the support member when its pawl is engaged. The first and second bridging parts may thus be moved apart readily to increase an extent of retraction. When it is wished to reduce the extent of retraction, the pawl of at least one of the first and second bridging parts is released from its cooperating set of teeth, as described above, to allow the separation between the first and second bridging parts to be reduced.

In another embodiment, the retractor comprises solely one bridging part. Each of the first to third anatomy engaging members may comprise a main body which is configured to engage with anatomy. The first to third anatomy engaging members may be configured such that adjacent main bodies are spaced apart from each other by about 120 degrees.

The support member and the second arm may be configured such that the support member rotates in relation to the second arm to thereby move the second arm along the support member.

The driver may comprise a first engaging portion and the support member may comprise a second engaging portion, the first and second engaging portions being configured to releasably inter-engage with each other to transmit movement of the driver to the support member. When it is desired to change a separation between the first and second arms, the driver may be brought into engagement with the support member. After operation of the driver, the driver may be disengaged from the support member.

Where the second arm is moved along the support member by rotation of the support member, the first and second engaging portions may be configured to releasably inter-engage with each other to impart rotation of the driver to the support member. The first engaging portion may be comprised in an end of the driver. The second engaging portion may be comprised in an end of the support member. The first and second engaging portions may define inter-locking profiles.

The driver may comprise a hand grippable part, such as a T-shaped handle, by which the driver may be rotated by a user. The retractor may be configured such that the hand grippable part and the support member rotate about the same axis.

The second arm may comprise a proximal portion comprising the threaded portion. The proximal portion may be configured to encircle the support member. The second arm may further comprise an elongate second arm member which extends from the proximal portion. The second arm member may be fixedly attached to the proximal portion. The proximal portion and the second arm member may be unitary. The proximal portion and the second arm member may be integrally formed.

The support member may define a second screw thread along part of its length and along a different part of the support member defining the first screw thread. The first screw thread and the second screw thread may be defined along adjacent parts of the support member. The support member may have first and second halves along its length with the first half defining the first screw thread and a second half of defining the second screw thread. The first arm may define a second threaded portion which cooperates with the second screw thread to move the second arm along the support member. The driver may be operable to move each of the first and second arms along the support member simultaneously whereby separation between the first and second arms changes by movement of both first and second arms. The first and second screw threads may run in opposite directions whereby movement and more specifically rotation of the support member relative to the first and second threaded portions causes the first and second arms to move in opposite directions.

The first arm may comprise a proximal portion comprising the second threaded portion. The proximal portion may be configured to encircle the support member.

The first arm may further comprise an elongate first arm member which extends from the proximal portion. The first arm member may be fixedly attached to the proximal portion. The proximal portion of the first arm and the first arm member may be unitary. The proximal portion of the first arm and the first arm member may be integrally formed.

The support member and the first and second arms may be configured such that the support member rotates in relation to the first and second arms to thereby move both of the first and second arms along the support member. As described above, the driver may engage with the support member to rotate the support member. The separation of the first and second arms may thus be changed.

At least one of the first and second arm members may be substantially elliptical in cross-section. A substantially elliptical cross-section has been found to provide an appropriate balance of resistance to torsion and lower bending stress. A ratio of width in cross section to height in cross section of the elongate first arm member may be between 1.5 and 2.5. More specifically the ratio of width in cross section to height in cross section of the elongate first arm member may be 2. For example, the width in cross section may be 20 mm and the height in cross section may be 10 mm.

The support member may comprise plural screw threads along a same part of its length. The threaded portion may be configured accordingly. On the one hand, increasing the number of screw threads increases the lead angle correspondingly and thereby increases the travel of the second arm along the support member per turn. On the other hand, increasing the number of screw threads reduces the likelihood of self-locking. Self-locking may be desirable to an extent to reduce the likelihood of the second arm being pushed or pulled along the support member. Accordingly, there may be compromise between providing for an extent of self-locking and extent of travel of the second arm per turn. In a form of the invention, the screw thread on the support member may have two starts.

An anatomy engaging member may be configured such that it extends substantially orthogonally to the arm or to a bridging part. The anatomy engaging member may be configured to attach releasably to an arm or to a bridging part. The anatomy engaging member may attach releasably to the arm or bridging part by an annular snap-fit. Snap-fit attachment may be by way of resilience of a part of the anatomy engaging member that fits over the arm or bridging part. More specifically the anatomy engaging member may define an engaging member profile which provides for mechanical engagement with an arm or with a bridging part. The engaging member profile and the arm or bridging part may be configured such that the anatomy engaging member is clipped onto the arm or bridging part. The engaging member profile may be configured in substantially the same fashion as the bridging part profile described above.

The anatomy engaging member may comprise a main body. The main body may have the form of an elongate plate. The elongate plate may be substantially rectangular. Furthermore, the main body may be concave in a direction of retraction but not biconcave. Where the retractor comprises four anatomy engaging members, the curved surfaces of the anatomy engaging members may define together a space of circular cross section, albeit a space with a gap between each pair of adjacent anatomy engaging members. A distal edge of the main body may define a nonlinear profile, such as a concave profile or a wave profile. The nonlinear profile may allow the anatomy engaging member to fit around a nonlinear profile defined by bony anatomy.

The retractor may be configured to hold apart two anatomical parts, such as vertebrae or muscle and tissue. The retractor may be a surgical retractor. More specifically the retractor may be a spinal retractor. Alternatively or in addition, the retractor may be configured for lumbar, cervical or thoracic discectomy, spinal decompression, laminectomy or foraminotomy.

At least a part of the retractor, such as the support member and the second arm, may be formed of a plastics material. More specifically the retractor may be formed substantially completely of a plastics material. X-rays may pass through plastics material. The retractor may therefore not obstruct the surgery site. The plastics material may comprise a polyamide and more specifically a partially aromatic polyamide, such as polyarylamide. The threaded portion may be formed at least in part of a different plastics material to other parts of the retractor. More specifically the second part may be formed at least in part from a thermoplastic polymer and more specifically a polyamide, such as nylon. Formation of the threaded portion from the like of nylon may provide for low friction movement of the second arm along the support member. Parts of the retractor may be integrally formed, such as by injection moulding. For example, the first and second arms may each be integrally formed. By way of further examples, the anatomy engaging member or the support member may be integrally formed.

According to a further aspect of the present invention there is provided a retractor comprising: an elongate support member having a screw thread along at least part of its length; a first arm having a first anatomy engaging member depending therefrom; a second arm having a second anatomy engaging member depending therefrom and a threaded portion which cooperates with the screw thread to move the second arm along the support member; and a driver operable to move the second arm along the support member by cooperation of the threaded portion and the screw thread whereby separation between the first and second arms changes.

Embodiments of the further aspect of the present invention may comprise one or more features of the first aspect of the present invention.

BRIEF DESCRIPTION OF DRAWINGS

Further features and advantages of the present invention will become apparent from the following specific description, which is given by way of example only and with reference to the accompanying drawings, in which.

DESCRIPTION OF EMBODIMENTS

Figure 1:
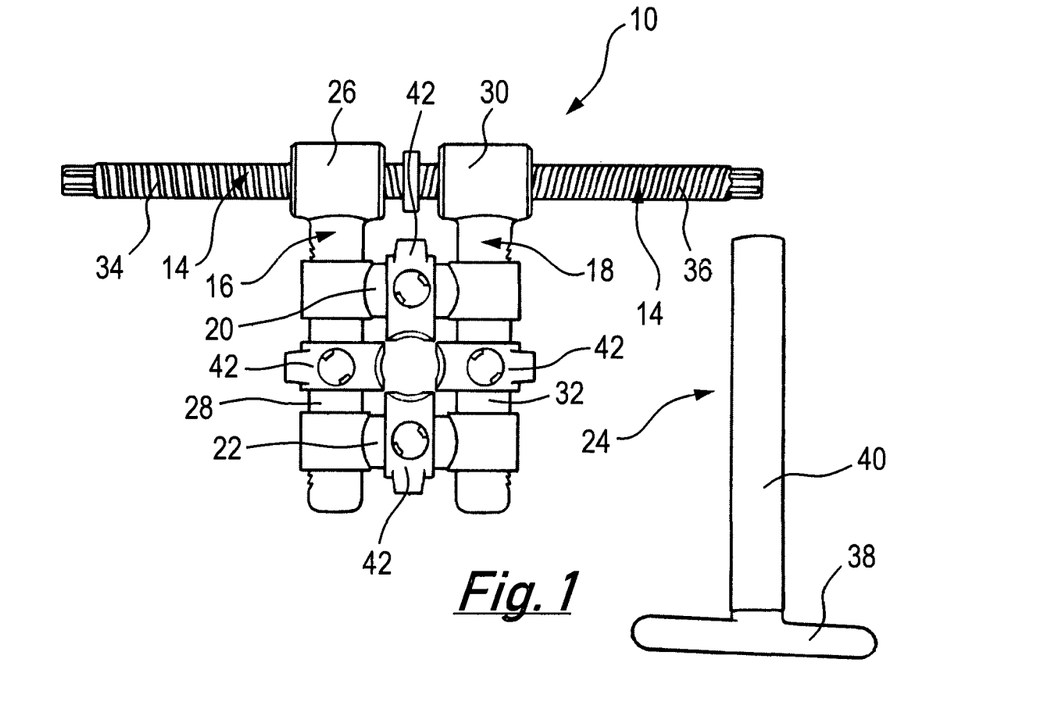
FIG. 1 is a view from above of a retractor according to an embodiment of the present invention.
Figures 2A, 2B:
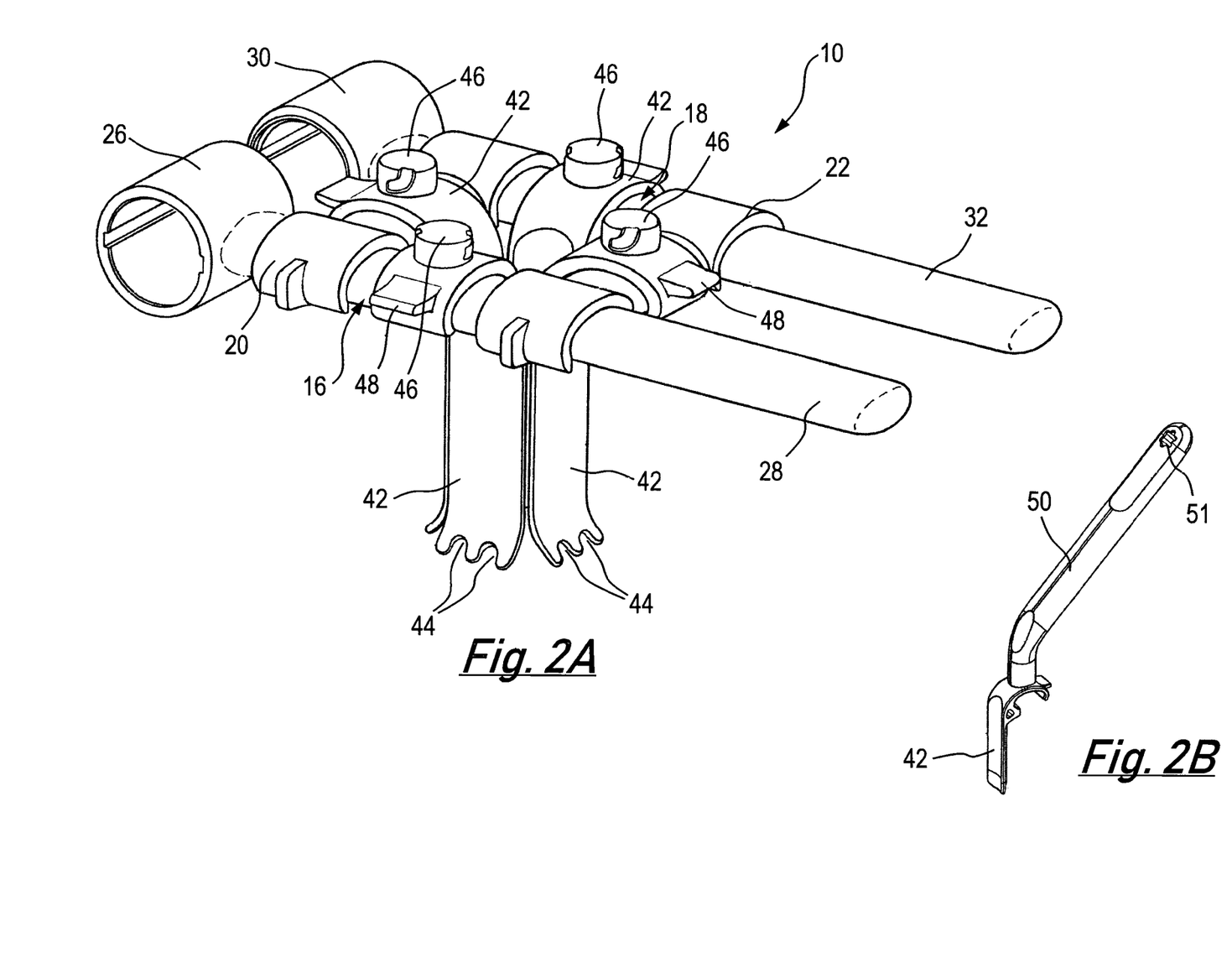
FIG. 2A is a perspective view of the retractor without the support member.
FIG. 2B is a perspective view of a rod attached to a blade.

A retractor 10 according to an embodiment of the present invention is shown from above in FIG. 1 and in perspective view in FIG. 2A. The retractor 10 comprises an elongate support member 14. The retractor 10 also comprises a first arm 16 and a second arm 18 each mounted for movement along the support member 14. The retractor 10 further comprises a first bridging part 20 and a second bridging part 22. The retractor 10 yet further comprises a driver 24.

The first arm 16 comprises a proximal portion 26 which encircles the support member 14 and an elongate first arm member 28 which extends from the proximal portion 26. The first arm member 28 is integrally formed with the proximal portion 26. The second arm 18 comprises a proximal portion 30 which encircles the support member 14 and an elongate second arm member 32 which extends from the proximal portion 30. The second arm member 32 is integrally formed with the proximal portion 30. As can be seen from FIG. 2A, the first and second arm members 28, 32 are substantially parallel. Each of the first and second arm members is substantially elliptical in cross-section. The width in cross section of each arm member is 20 mm and the height in cross section is 10 mm.

One half of the exterior of the support member 14 defines a first screw thread 34 and the other half of the exterior of the support member 14 defines a second screw thread 36. The first and second screw threads 34, 36 run in opposite directions such that each runs towards its respective end of the support member 14. Each of the first and second screw threads 34, 36 has two starts. The interior of each of the two proximal portions 26, 30 defines a threaded portion which engages mechanically with a respective one of the first and second screw threads 34, 36. As will become more fully apparent from the following description, rotation of the support member 14 about its longitudinal axis moves each of the first and second arms 16, 18 in opposite directions along the support member 14 (i.e. together or apart) by virtue of cooperation of the threaded portion on each proximal portion 26, 30 with a respective one of the first and second screw threads 34, 36.

The driver 24 comprises a T-shaped handle 38 mounted on a first end of a handle shaft 40. The second opposite end of the handle shaft 40 is releasably attached to an end of the support member 14 by way of a first releasable coupling part in the form of a shaped recess in the second end of the handle shaft 40 and a second releasable coupling part in the form of a correspondingly shaped protrusion on each of both ends of the support member 14. When driver 24 is fitted to an end of the support member 14, the first and second releasable coupling part interlock to impart rotation of the driver to the support member. Rotation of the T-shaped handle 38 thus causes rotation of the support member 14 whereby separation between the first and second arms 16, 18 changes. Where lighter loads on the first and second arms 16, 18 are being driven, the driver 24 is not required and the support member 14 is rotated by hand. In another un-illustrated embodiment, the handle shaft 40 comprises a universal joint whereby the handle 38 is rotated about an axis at an angle to the axis about which the support member 14 rotates.

Each of the first and second bridging parts 20, 22 is releasably attached to the first and second arms 16, 18 at locations spaced apart along the first and second arms. Furthermore, the first and second bridging parts 20, 22 are movable along the first and second arms 16, 18. The first and second bridging parts 20, 22 are described in more detail below.

The retractor 10 further comprises four blades 42 (which constitute anatomy engaging members). As can be seen from FIGS. 1 and 2, a first one of the blades 42 is attached to the first arm 16 and a second one of the blades 42 is attached to the second arm 18 whereby each blade depends substantially orthogonally from its respective arm. A third one of the blades 42 is attached to the first bridging part 20 and a fourth one of the blades 42 is attached to the second bridging part 22 whereby each blade depends substantially orthogonally from its respective bridging part. The four blades 42 provide for retraction in a first direction parallel to the longitudinal axis of the support member 14 by rotation of the support member and in a second direction substantially orthogonal to the first direction by way of movement apart of the first and second bridging parts 20, 22.

Each blade 42 defines an engaging member profile at its proximal end whereby the blade is clipped to and thereby releasably engaged with an arm while allowing for movement of the blade along the arm when attached to the arm. The shape of the engaging member profile is the same as the bridging part profile described below. Each blade 42 defines two recesses 44 in a distal end of a main body of the blade with the two recesses being spaced apart across the width of the main body. The main body of the blade has the form of a substantially rectangular plate which defines a curve across its width. As may be seen from FIG. 1, the curved surfaces of the four blades 42 define together a space of circular cross section, albeit a space with a gap between each pair of adjacent blades.

Referring to FIG. 2A, each blade 42 has a cylindrical locking member 46 extending from the upper surface of the proximal end of the blade. Rotation of the cylindrical locking member 46 relative to the rest of the blade locks and unlocks the telescopic first and second bridging part components in respect of their telescopic movement. The first and second bridging part components are described further below. The cylindrical locking member 46 is rotated by a rod having an end shaped to fit over the cylindrical locking member and to inter-engage with profiles defined in the side of the cylindrical locking member. The rod 50 is shown in FIG. 2B when attached to a blade 42 by way of the cylindrical locking member 46. Inter-engagement of the end of the rod 50 with profiles defined in the side of the cylindrical locking member enables torque to be transmitted from the rod to the cylindrical locking member 46. When attached to the cylindrical locking member 46, the rod 50 is also used to clip the blade 42 onto and off an arm or bridging part by applying torque around the arm or the bridging part. As can be seen from FIG. 2B, the end 51 of the rod 50 opposite the end that fits over the cylindrical locking member 46 has a star shaped bore therethrough which is shaped to fit over and inter-engage with an end of the support member 14. The rod 50 can thus be used instead of the handle 38 to rotate the support member 14 to thereby change the separation of the first and second arms. A thumb sized tab 48 extends from the side of the proximal end of each blade 42. Instead of using the rod, the thumb sized tab 48 is pressed manually in one direction or the other to clip the blade 42 onto or off the arm or bridging part.

The retractor 10 is formed substantially completely of a plastics material. Most of the retractor 100 is formed from a polyarylamide. By way of exception, the threaded profile of each proximal portion 26, 30 is formed from nylon. More specifically a collar formed of nylon that defines the threaded profile on its interior surface is received in and clipped into place within a bore defined by the proximal portion 26, 30. According to another form, the threaded profile of each proximal portion 26, 30 is formed from a polyarylamide whereby there is no need for the collar. Parts of the retractor are integrally formed by injection moulding. For example, the first and second arms 16, 18 are each integrally formed. By way of further example, the handle 38 and the handle shaft 40 are formed integrally together.

Figure 3A:
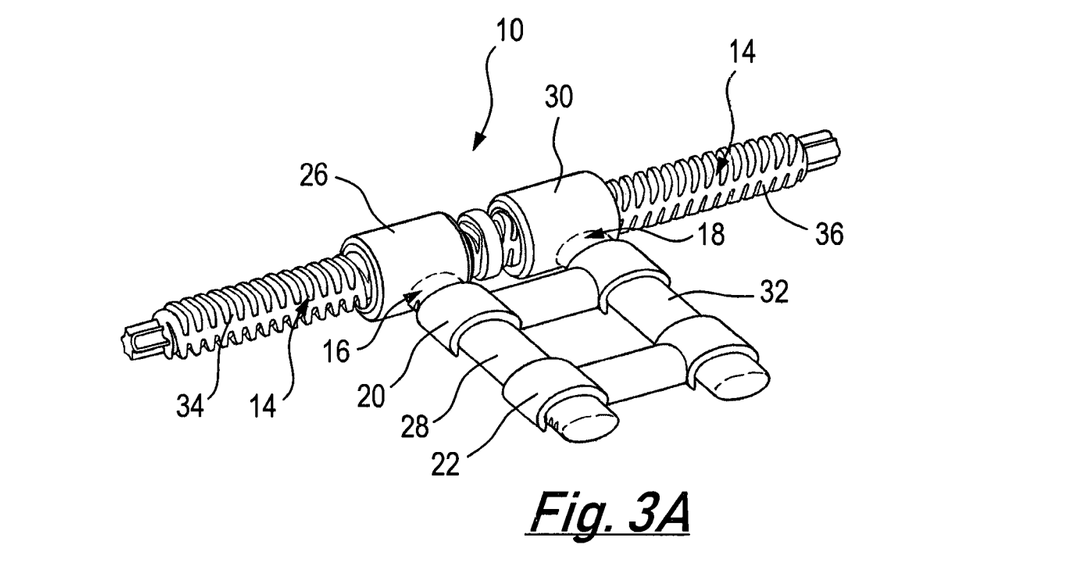
FIG. 3A is a perspective view of the retractor without the blades.
Figure 3B:
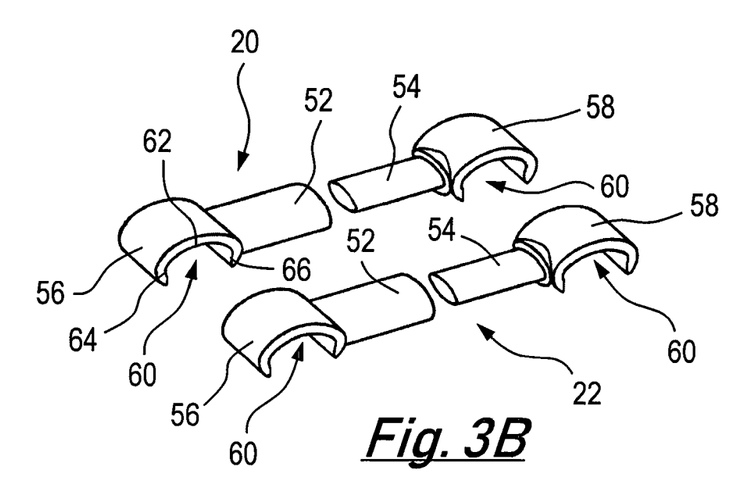
FIG. 3B is a perspective of the bridging parts.

A perspective view of the retractor 10 without the blades is shown in FIG. 3A with the first and second bridging parts shown alone in FIG. 3B. Components in common with the retractor shown in FIGS. 1 and 2 are designated in FIG. 3A and FIG. 3B with like reference numerals. The reader's attention is directed to the description provided above with reference to FIGS. 1 and 2 for description of such components in common. As may be seen from FIG. 3B, the first and second bridging parts 20, 22 are the same. Each of the first and second bridging parts 20, 22 comprises a first bridging part component 52 and a second bridging part component 54. A proximal end of the first bridging part component 52 defines a bore which is shaped to receive a proximal end of the second bridging part component 54 to thereby provide for change in length of the bridging part 20, 22 by telescopic adjustment. As the separation of the first and second arms 16, 18 is increased by rotation of the support member 14, the proximal end of the second bridging part component 54 is withdrawn from the bore defined in the end of the first bridging part component 52. As the separation of the first and second arms 16, 18 is decreased by rotation of the support member 14 in the opposite direction, the proximal end of the second bridging part component 54 is received further in the bore defined in the end of the first bridging part component 52.

As described above, each bridging part 20, 22 is configured to releasably attach at each of its first and second ends to a respective arm 16, 18. Each of the first and second ends 56, 58 of the bridging part may define a bridging part profile 60 which cooperates with the profile of the arm to resist separation of the bridging part from the arm. The bridging part profile 60 has a main profile portion 62 which extends across the upper surface of the arm. The bridging part profile 60 also has first and second lateral portions 64, 66 at a respective end of the main profile portion 62 which are each shaped to extend over a side of the arm and then a short distance across the lower surface of the arm. The distal end of the first lateral portion 64 therefore opposes the distal end of the second lateral portion 66 with the distal ends of the first and second lateral portions being spaced apart from each other across the lower surface of the arm. The bridging part 20, 22 is attached to an arm 16, 18 by sliding the bridging part profile 60 over the distal end of the arm. Alternatively and in view of the bridging part 20, 22 being formed from a resilient material, the end of the bridging part 56, 58 is pressed against the upper surface of the arm whereby the distal ends of the first and second lateral portions 64, 66 are forced apart to an extent sufficient to admit the arm to the space defined by the bridging part profile 60. When the arm is admitted properly in the space defined by the bridging part profile 60, the distal ends of the first and second lateral portions 64, 66 move together again under bias exerted by the resilient material whereby the bridging part 20, 22 is attached securely to the arm 16, 18 whilst allowing for movement of the bridging part along the arm.

Figure 4:
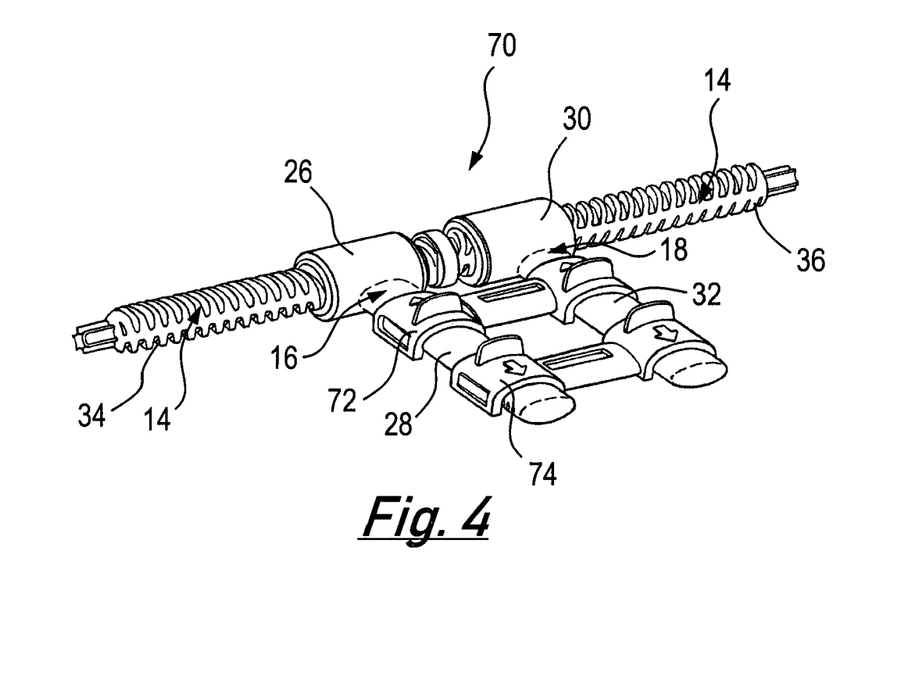
FIG. 4 is a perspective view of a retractor according to another embodiment of the present invention without the blades.

A retractor 70 according to another embodiment of the present invention is shown in FIG. 4 without the blades. Components in common with the retractor shown in FIGS. 1, 2, 3A and 3B are designated in FIG. 4 with like reference numerals. The reader's attention is directed to the description provided above with reference to FIGS. 1, 2, 3A and 3B for description of such components in common. Differences in respect of the embodiment of FIG. 4 will now be described.

The retractor 70 of FIG. 4 comprises first and second bridging parts 72, 74 of different form to the first and second bridging parts 20, 22 described above. The first and second bridging parts 72, 74 of FIG. 4 releasably attach to a respective arm and support a blade as described above. A perspective view of an arm and a part of each of the two bridging parts of the retractor of FIG. 4 are shown in more detail in FIG. 5A. Parts in common with the arm and bridging parts shown in FIG. 4 are designated in FIG. 5A with like reference numerals. Each of the first and second bridging parts 72, 74 comprises a tab 76 extending from its upper surface. The tab 76 is of a size that it may be gripped by a user, such as between finger and thumb, to thereby provide for ease of movement of the bridging part 72 along the arm.

Figure 5A:
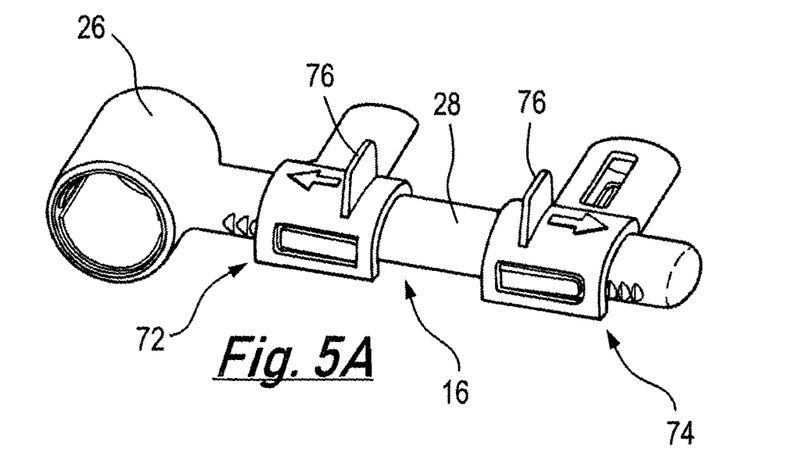
FIG. 5A is a perspective view of an arm and a part of each of two bridging parts.
Figure 5B:
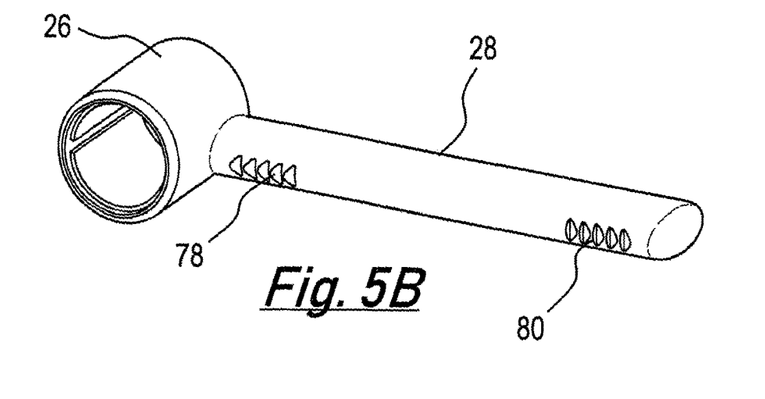
FIG. 5B is a perspective view of the arm of FIG. 5A.

As may be seen from FIG. 5A and more clearly from FIG. 5B, which is a perspective view of the arm of FIG. 5A alone, a first set of teeth 78 and a second set of teeth 80 are defined in a side of the arm 28. The first set of teeth 78 extend along a proximal part the arm 28 where the first bridging part 72 is located and the second set of teeth 80 extend along a distal part the arm 28 where the second bridging part 74 is located. As may be seen from FIG. 5A and more clearly from FIG. 5C, which is a detailed perspective view of the second bridging part 74, the end of the second bridging part comprises a finger 82 cut out from the body of the bridging part and which remains attached at one end only to the body of the bridging part to define a living hinge. Although not shown in FIGS. 5A and 5C, the distal end of the finger 82 defines a protrusion which extends into the space defined by the bridging part profile 60. The finger 82 constitutes a pawl. The protrusion is located such that it is urged towards the second set of teeth 80 extending along the arm by the spring bias exerted by the finger 82.

Figure 5C:
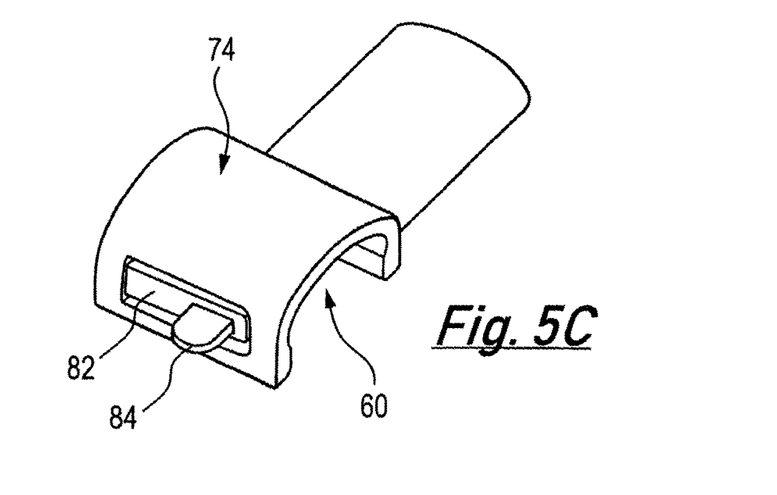
FIG. 5C is a perspective view of a part of a bridging part according to another embodiment.

The teeth in the second set of teeth 80 are shaped to allow for movement of the pawl constituted by the finger 82 over the teeth and hence the bridging part in a first direction away from the support member. The teeth in the second set of teeth 80 are further shaped such that the pawl constituted by the finger 82 bears against a surface of a tooth to thereby resist movement of the bridging part in a second direction towards the support member. If the user wishes to move the bridging part 74 towards the support member, the user grips a tab 84 extending from an exterior surface of the finger 82 and pulls the finger and hence the protrusion against the spring bias away from the second set of teeth 80 to thereby release the bridging part for movement towards the support member. The first set of teeth 78 are similarly shaped to the second set of teeth 80 but with the exception that teeth in the first set are oppositely directed to teeth in the second set whereby the first bridging part 72 is movable towards the support member when the pawl is engaged and movable away from the support member only when the pawl of the first bridging part is disengaged by the user.

The invention claimed is:

1. A retractor comprising:
an elongate support member having a screw thread along at least part of its length;
a first arm having a first anatomy engaging member depending therefrom;

a second arm having a second anatomy engaging member depending therefrom and a threaded portion which cooperates with the screw thread to move the second arm along the support member;

a driver operable to move the second arm along the support member by cooperation of the threaded portion and the screw thread whereby separation between the first and second arms changes;

a first bridging part attached towards a first end thereof to the first arm and attached towards a second, opposite end thereof to the second arm, the first bridging part having a third anatomy engaging member depending therefrom;

a second bridging part having a fourth anatomy engaging member depending therefrom, the second bridging part attached towards a first end thereof to the first arm at a location spaced apart from the first bridging part and attached towards a second end thereof to the second arm at a location spaced apart from the first bridging par whereby the second bridging part is substantially parallel to the first bridging part, the second bridging part movable on the first and second arms while the second bridging part is attached to the first and second arms;

a first ratchet mechanism regulating movement of the first bridging part along the first and second arms; and a second ratchet mechanism regulating movement of the second bridging part along the first and second arms, wherein each of the first, second, third, and fourth anatomy engaging members comprises a blade having an attached end attached to a corresponding arm or bridging part, and a free end extending from the attached end, the first ratchet mechanism has a first set of teeth and the second ratchet mechanism has a second set of teeth, and teeth of the first set of teeth are oppositely directed to teeth of the second set of teeth whereby movement of the first and bridging parts together is resisted.

2. The retractor according to claim 1, wherein the support member is of substantially cylindrical form with the screw thread defined on the surface of the support member, and each of the first and second arms is mounted on and extends away from the support member.

3. The retractor according to claim 1, wherein the first bridging part is movable on the first and second arms while the first bridging part is attached to the first and second arms whereby the retractor is configured to provide for retraction along two different directions by way of the first to fourth anatomy engaging members.

4. The retractor according to claim 3, wherein separation between the first and second ends of the first bridging part is changeable hereby a length of the first bridging part is changeable.

5. The retractor according to claim 1, wherein the first bridging part is configured to releasably attach at each of its first and second ends to a respective one of the first and second arms.

6. The retractor according to claim 5, wherein the first bridging part releasably attaches to the arm by an annular snap-fit of an end of the first bridging part over the arm.

7. The retractor according to claim 1, wherein at least one of the first and second sets of teeth are defined along at least a part of an arm, and a pawl of the respective ratchet mechanism is comprised in an end of the respective bridging part.

8. The retractor according to claim 7, wherein the pawl comprises a protrusion which is configured to be gripped and moved by a user, whereby the pawl is released from the teeth against a spring bias.

9. The retractor according to claim 1, wherein the support member rotates in relation to the second arm to thereby move the second arm along the support member, rotation of the support member being driven by the driver.

10. The retractor according to claim 9, wherein the driver is a component apart from the support member, the driver comprises a first engaging portion and the support member comprises a second engaging portion, the driver being brought into use by removable inter-engagement of the first and second engaging portions with each other whereby rotation of the driver is transmitted to the support member.

11. The retractor according to claim 1, wherein the second arm comprises a second arm proximal portion and an elongate second arm member extending from the second arm proximal portion, an inner surface of the second arm proximal portion encircling the support member, the threaded portion being defined on the inner surface of the second arm proximal portion.

12. The retractor according to claim 11, wherein the first arm comprises a first arm proximal portion and an elongate first arm member extending from the first arm proximal portion, an inner surface of the first arm proximal portion encircling the support member, a second threaded portion being defined on the inner surface of the first arm proximal portion, the support member defining a second screw thread along part of its length, the first screw thread and the second screw thread defined along adjacent longitudinal parts of the support member, the second threaded portion cooperating with the second screw thread to move the first arm the support member.

13. The retractor according to claim 12, wherein the support member rotates in relation to the first and second arms, the first and second screw threads running in opposite directions whereby rotation of the support member in one direction moves the first and second arms along the support member simultaneously and in opposite directions.

14. The retractor according to claim 1, wherein each of the first and second arm members is substantially elliptical in cross-section.

15. The retractor according to claim 1, wherein the screw thread on the support member has two starts.

16. The retractor according to claim 1, wherein each of the anatomy engaging members is attached releasably to the corresponding arm or bridging part by an annular snap-fit of the attached end of the anatomy engaging member over the corresponding arm or bridging part.

17. The retractor according to claim 1, wherein each of the anatomy engaging members comprises a main body, a distal edge of at least one of the main bodies defines a nonlinear profile whereby the anatomy engaging member fits around a nonlinear profile defined by bony anatomy.

* * * * *